United States Patent [19]

Blanc

[11] Patent Number: 4,595,751
[45] Date of Patent: Jun. 17, 1986

[54] PERHYDRO-[2,3-C]-OXAZOLO-1,4-OXAZINES AND THEIR PROCESS OF PREPARATION

[75] Inventor: Alain Blanc, Paris, France

[73] Assignee: Societe Francaise Hoechst, Puteaux, France

[21] Appl. No.: 713,797

[22] Filed: Mar. 20, 1985

[30] Foreign Application Priority Data

Mar. 26, 1984 [FR] France .................. 84 04655

[51] Int. Cl.$^4$ .................................. C07D 498/04
[52] U.S. Cl. .................................. 544/105; 562/567
[58] Field of Search .......................... 544/105

[56] References Cited

FOREIGN PATENT DOCUMENTS 2713574 10/1978 Fed. Rep. of Germany .
926313 5/1963 United Kingdom .
565034 7/1977 U.S.S.R. .

OTHER PUBLICATIONS

Laurent et al., Bull. Soc. Chim., (1978), pp. 83–88.

*Primary Examiner*—Richard L. Raymond
*Attorney, Agent, or Firm*—Sheridan Neimark

[57] ABSTRACT

Novel perhydro-[2,3-c]-oxazolo-1,4-oxazines, having the general formula (I):

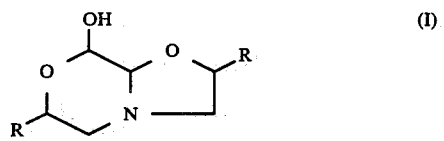

in which R represents a hydrogen atom or a $C_1$–$C_5$-alkyl radical, and the process for preparation thereof comprising reacting at a temperature lower than 30° C. one mole of glyoxal with one mole of diethanolamine having the general formula (II):

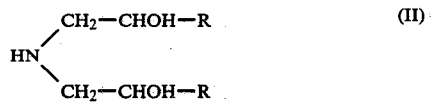

in which R has the same meaning as above.

7 Claims, No Drawings

PERHYDRO-[2,3-C]-OXAZOLO-1,4-OXAZINES AND THEIR PROCESS OF PREPARATION

This invention relates to novel perhydro-[2,3-c]-oxazolo-1,4-oxazines, their preparation and application to obtaining substituted glycines.

The novel perhydro-[2,3-c]-oxazolo-1,4-oxazines according to the invention are the compounds having the general formula (I):

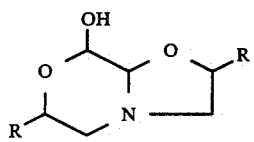

in which R represents a hydrogen atom or a $C_1$–$C_5$-alkyl radical.

The term "$C_1$–$C_5$-alkyl" may designate for example a methyl, ethyl, n-propyl, isopropyl, n-butyl, isobutyl, tertiobutyl, pentyl radical.

There can be cited as specific examples of compounds according to the invention in particular the following: 7-hydroxy-perhydro-[2,3-c]-oxazolo-1,4-oxazine and 2,5-dimethyl-7-hydroxy-perhydro-[2,3-c]-oxazolo-1,4-oxazine.

Federal Republic of Germany patent application No. 2 713 574 describes 7-hydroxy-perhydro-[2,3-c]-oxazolo-1,4-oxazines substituted on summits 7 and 7a by identical or different radicals selected among the group comprising aliphatic, cyclo-aliphatic, aromatic, arylaliphatic radicals, or possibly by an alkylene radical fixing an aliphatic cycle between these two summits. These products are obtained by the action of a suitably substituted diethanolamine over an alphadiketone such as 1,2-cyclohexanedione, benzil, diacetyl, at a temperature of between $-20°$ and $200°$ C., advantageously on toluene reflux in the presence of a catalytic quantity of paratoluene-sulfonic acid and concomitant distillation of the formed water.

In British Pat. No. 926 313 it is also stated that cold condensation of three moles of glyoxal with one mole of diethanolamine leads to an addition compound (adduct) crystallized and pale yellow presenting a melting point of $100°$–$110°$ C., and a micro-analysis according with formula $C_{10}H_{17}NO_8$, $H_2O$, 8%.

It is known moreover that glyoxal reacts with N-alkyl-ethanolamines, either under cold conditions to preferentially lead to a 3,3'-dialkyl-2,2'-bisoxazolidine (P. A. Laurent et al. Bull. Soc. Chim., France, 1978 II, 83–88), or hot conditions to lead to a 4,8-dialkyl-perhydro-[3,2-b]-1,4-oxazino-1,4-oxazine (Soviet Union Pat. No. 365 034).

The Applicant however has discovered in a totally unexpected manner that the products having the general formula (I) above are easily formed by a process characterized by reacting at a temperature lower than $30°$ C. one mole of glyoxal with one mole of diethanolamine having the general formula (II):

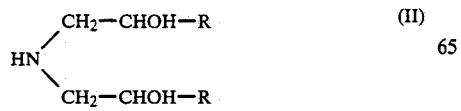

in which R has the meaning given above to obtain a corresponding product having the formula (I).

Under the preferential conditions for carrying out the invention the above process is realized:
at a temperature of between $0°$ C. and $10°$ C.;
in aqueous medium;
starting from glyoxal in aqueous solution of a concentration by weight of between 40 and 55%;
by following the consumption of the diethanolamine having the general formula (II) through potentiometric dosage from test samples regularly removed from the reactional medium.

The products having the general formula (I) above are generally little soluble in water and usually they spontaneously crystallize in their preparation medium.

In aqueous solution, they are little stable and hydrolyze into the corresponding N,N-bis-(2-hydroxy-alkyl)-glycine having the general formula (III)

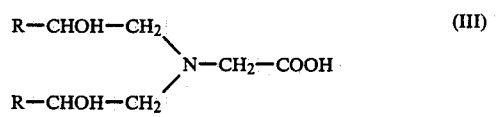

in which R has the meaning given above.

The higher the hydrolysis temperature, the quicker such hydrolysis. At $100°$ C. a transformation rate of 50% is reached in 2 minutes and of 100% in 20 minutes. At $60°$ C. in 30 minutes there is only obtained 20% of transformation.

This easy transformation of products having the formula (I) above to corresponding glycines having the formula (III) offers interesting application possibility for these products and is another object of the invention.

The glycines having the formula (III) and in particular N,N-bis-(2-hydroxy-ethyl)-glycine are products presenting precious chelating or complexing properties broadly described in the literature.

According to this invention, the hydrolysis is effected by heating on reflux in water a product having the general formula (I). Such reaction is readily followed by potentiometric analysis of test samples regularly removed from the reactional medium. When the transformation rate approaches 100%, the desired acid is isolated by known means.

The object of this invention is more especially a process for preparation of N,N-bis-(2-hydroxy-ethyl)-glycine and N,N-bis-(2-hydroxy-2-methyl-ethyl)-glycine. This process is characterized by heating at a temperature higher than $60°$ C. in aqueous medium a product having the formula (I) above to obtain a corresponding glycine having the formula (III) which is isolated by known means.

The following examples are given by way of illustration and do not intend to limit the invention in any way.

EXAMPLE 1

105.14 g (one mole) of diethanolamine are introduced at $10°$ C. in 30 minutes under stirring into 145 g (one mole) of glyoxal at 40% by weight in water. A light yellow solution is obtained. At this stage, potentiometric dosage effected on a test sample determines a transformation rate of 95%.

The solution is then cooled to $0°$ C., the desired product spontaneously crystallizes; it is squeezed out, then dried under vacuum at 30° C. at constant weight in the presence of diphosphorous pentaoxide.

Thus, 84.2 g (0.58 mole) of 7-hydroxy-perhydro-[2,3-c]-oxazolo-1,4-oxazine are isolated in form of colorless crystals having a melting point of 113° C. and a pK of 4.7. This product is soluble at 4% in water at 20° C. and at 50% at 100° C.; solubility in methanol at 20° C. is 27%, and 100% on reflux.

| Micro-analysis | C % | H % | N % | O % |
|---|---|---|---|---|
| C₆H₁₁NO₃ calculated | 49.64 | 7.64 | 9.65 | 33.07 |
| P.M. 145.15 found | 49.5 | 7.7 | 9.9 | |

Physical analyses

Infrared: absence of carbonyl
NMR of proton at 500 MhZ (solvent DMSO)
Chemical shifts, δppm relative to TMS.

| | δ | | | | | | | | |
|---|---|---|---|---|---|---|---|---|---|
| $H_a$ | 2.506 | m 1H | $J_{Ha-Hb}$ = | 11.1 Hz, | $J_{Ha-He}$ = | 3.7 Hz, | $J_{Ha-Hj}$ = | 2.7 Hz | |
| $H_b$ | 2.642 | m 1H | $J_{Hb-Ha}$ = | 11.1 Hz, | $J_{Hb-Hj}$ = | 9.1 Hz, | $J_{Hb-He}$ = | 3.7 Hz | |
| $H_c$ | 2.915 | m 1H | $J_{Hc-Hd}$ = | 11.1 Hz, | $J_{He-Hf}$ = | 8.9 Hz, | $J_{He-Hg}$ = | 8.9 Hz | |
| $H_d$ | 3.078 | m 1H | $J_{Hd-Hc}$ = | 11.1 Hz, | $J_{Hd-Hg}$ = | 7.0 Hz, | $J_{Hd-Hf}$ = | 2.7 Hz | |
| $H_e$ | 3.434 | m 1H | $J_{He-Hj}$ = | 11.5 Hz, | $J_{He-Ha}$ = | 3.7 Hz, | $J_{He-Hb}$ = | 3.7 Hz | |
| $H_f$ | 3.565 | m 1H | $J_{Hf-Hc}$ = | 8.9 Hz, | $J_{Hf-Hg}$ = | 7.3 Hz, | $J_{Hf-Hd}$ = | 2.7 Hz | |
| $H_g$ | 3.703 | m 1H | $J_{Hg-Hc}$ = | 9.1 Hz, | $J_{Hg-Hf}$ = | 7.3 Hz, | $J_{Hg-Hd}$ = | 7.0 Hz | |
| $H_h$ | 3.715 | d 1H | $J_{Hh-Hl}$ = | 2.1 Hz | | | | | |
| $H_j$ | 3.887 | m 1H | $J_{Hj-He}$ = | 11.5 Hz, | $J_{Hj-Hb}$ = | 9.1 Hz, | $J_{Hj-Ha}$ = | 2.7 Hz | |
| $H_l$ | 4.812 | d 1H | $J_{Hl-Hh}$ = | 2.1 Hz | | | | | |

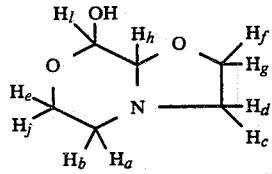

To the Applicant's knowledge, this product is not described in the literature.

EXAMPLE 2

It is proceeded as in Example 1, but diethanolamine is replaced with bis-(2-hydroxy-propyl)-amine. Upon completing the introduction of hydroxylated amine the measured transformation rate from a test sample by potentiometric dosage is 98%.

Thereafter 69.3 g (0.5 mole) of 7-hydroxy-2,5-dimethyl-perhydro-[2,3-c]-oxazolo-1,4-oxazine is isolated in form of colorless crystals presenting a melting point of 119° C. and a pK of 4.1.

| Micro-analysis. | C % | H % | N % | O % |
|---|---|---|---|---|
| C₈H₁₅NO₃ calculated | 55.47 | 8.73 | 8.09 | 27.71 |
| P.M. 173.21 found | 55.3 | 8.9 | 7.7 | |

Physical infrared analysis: absence of carbonyl.
To the Applicant's knowledge, this product is not described in the literature.

EXAMPLE 3

There is heated for 1 hour on reflux:
14.5 g (0.1 mole) of 7-hydroxy-perhydro-[2,3-c]-oxazolo-1,4-oxazine in 30 g of water.
Then, the obtained solution is cooled to the ambient temperature.

By adding ethanol thereto, the desired product crystallizes. It is squeezed out, then dried at constant weight under vacuum at 100° C.

There is thus obtained 13.5 g (0.083 mole) of crystallized N,N-bis-(2-hydroxy-ethyl)-glycine having a melting point of 193° C.

EXAMPLE 4

There is heated for 1 hour on reflux:
17.3 g (0.1 mole) of 2,5-dimethyl-7-hydroxy-perhydro-[2,3-c]-oxazolo-1,4-oxazine in 35 g of water.
Then, the obtained solution is cooled to the ambient temperature.

By addition of ethanol thereto, the desired product crystallizes. It is squeezed out, then dried at constant weight under vacuum at 60° C.

Thus, 16.5 g (0.086 mole) of crystallized N,N-bis-(2-hydroxy-propyl)-glycine are obtained having a melting point of 145°–146° C.

It will be understood that this invention was only described in a purely illustrative and not at all limitative manner and that any useful modification can be entered therein without however departing from its scope.

I claim:

1. Perhydro-[2,3-c]-oxazolo-1,4-oxazine having the general formula (I):

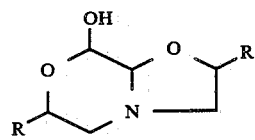

in which R represents a hydrogen atom or a C₁–C₅-alkyl radical.

2. 7-hydroxy-perhydro-[2,3-c]-oxazolo-1,4-oxazine.

3. 2,5-dimethyl-7-hydroxy-perhydro-[2,3-c]-oxazolo-1,4-oxazine.

4. A process for obtaining compounds such as defined in the general formula (I) of claim 1, comprising reacting at a temperature lower than 30° C. one mole of glyoxal with one mole of diethanolamine of the general formula (II):

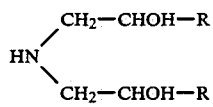 (II)

in which R has the meaning given for formula (I) of claim 1.

5. A process according to claim 4, carried out in water.

6. A process according to claim 4, wherein the compounds having the formula (II) is diethanolamine itself, thereby giving 7-hydroxy-perhydro-[2,3-c]-oxazolo-1,4-oxazine.

7. A process according to claim 4, wherein the compounds having the formula (II) is bis-(2-hydroxypropyl)-amine, thereby giving 7-hydroxy-2,5-dimethyl-perhydro-[2,3-c]-oxazolo-1,4-oxazine.

* * * * *